Figure 1:
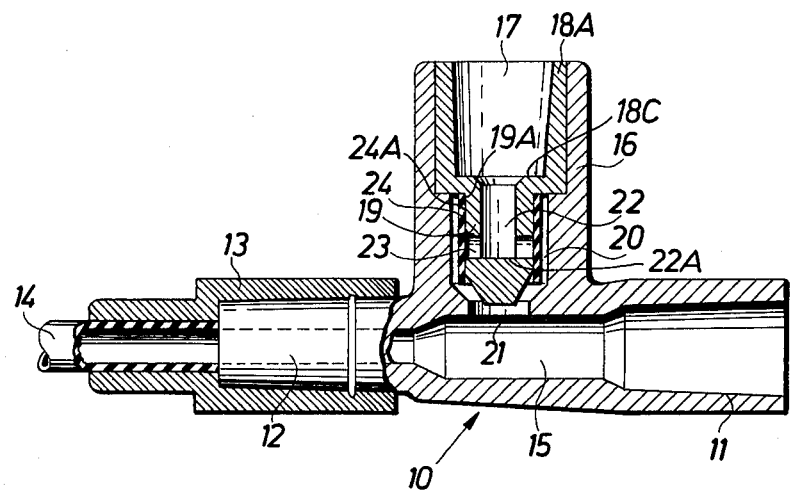

United States Patent

Ulinder

[11] 4,063,555
[45] Dec. 20, 1977

[54] CANNULA ASSEMBLY
[75] Inventor: Bjorn Ulinder, Saltsjoduvnas, Sweden
[73] Assignee: Aktiebolaget Stille-Werner, Stockholm, Sweden
[21] Appl. No.: 651,483
[22] Filed: Jan. 22, 1976
[30] Foreign Application Priority Data
  Jan. 24, 1975    Sweden .............................. 7500773
[51] Int. Cl.² .............................................. A61M 5/14
[52] U.S. Cl. .................. 128/214 R; 128/274; 137/604; 137/583
[58] Field of Search ................ 128/214 R, 214.4, 227, 128/274, 349 BV, 348; 137/604, 853
[56] References Cited
  U.S. PATENT DOCUMENTS
  2,551,315  5/1951  Christopher et al. ................. 128/227
  3,416,567  12/1968  Dardel et al. ..................... 128/274 X
  3,730,186  5/1973  Edmunds et al. .................... 128/325

FOREIGN PATENT DOCUMENTS
  733,890  7/1955  United Kingdom .......... 128/349 BV

*Primary Examiner*—Dalton L. Truluck

[57] ABSTRACT

A cannula is provided for administration of a fluid from two separate sources of supply, such as from an infusion fluid container and an injection syringe, comprising, in combination, a housing, a fluid flow passage therethrough having two fluid inlets and one fluid outlet, one of the fluid inlets being shaped to receive delivery means of an injection device for delivery of fluid to the cannula fluid flow passage, and having a check valve therein compelling flow therethrough only in the inward direction, and means in the one inlet positioned to accept any impact of the delivery means when inserted in the one inlet, and inhibit impact injury to the check valve upon such insertion.

10 Claims, 2 Drawing Figures

CANNULA ASSEMBLY

A cannula assembly is described in Swedish Pat. No. 211,721 which is intended to introduce an injection fluid into a cannula connected to an infusion fluid container, such as (for example) a vein cannula. The device is intended to be inserted in the line between the vein cannula and the connection to the infusion fluid container. The device has a housing with a through fluid flow passage, and a side inlet opening partway along the cannula fluid passage, for entry of injection fluid. The inlet opening has a conical nipple, designed for connection to the outlet cone of an injection syringe. The check valve body is of flexible material, and is disposed in the through flow passage of the cannula, sealingly overlying the side inlet opening, but adapted to be forced away from sealing engagement across the opening upon application thereto of a sufficiently high injection fluid pressure from the side inlet. In a preferred embodiment, the check valve is a sleeve-shaped extension of a tube which is the part of the connection to the infusion fluid container.

This device has the disadvantage that if the injection syringe has a needle tip, upon insertion of the syringe in the inlet opening the needle may puncture the check valve body or otherwise damage it.

In accordance with the invention, a cannula is provided for administration of a fluid from two separate sources of supply, such as from an infusion fluid container and an injection syringe, and is constructed so as to avoid this difficulty. The cannula of the invention comprises in combination, a housing; a fluid flow passage therethrough having two fluid inlets, one for one fluid and one for another fluid, and one fluid outlet; one of the fluid inlets being shaped to receive delivery means of a device for introduction of fluid to that inlet, and thus to the cannula fluid flow passage, and having a check valve therein compelling flow therethrough only in the inward direction; and means in the one inlet positioned to accept any impact of the delivery means when inserted in the one inlet, and inhibit impact injury to the check valve upon such insertion.

In a preferred embodiment, the one inlet is cup-shaped, with side and end walls of relatively hard material, such as plastic or metal, with the inlet opening in alignment with the end cup, so that the cup end receives any impact of the delivery means (such as a syringe needle) when inserted in the inlet. The fluid flow connection between the inlet and the cannula fluid flow passage is provided in the sides of the cup, in the form of one or several openings therethrough, and the check valve or check valves sealingly closes off the one or several such openings.

A preferred form of check valve is of resilient material, such as resilient plastic or rubber, tightly and sealingly engaging the outside of the cup inlet, thus closing off the side openings therein, and is adapted to move away from and open the openings upon application of a sufficient fluid pressure in the cup inlet, such as upon delivery of fluid thereto from an injection device.

The inlet opening is preferably shaped so as to receive the delivery means and/or fluid introduction device, such as the tip of an injection syringe, in a manner to permit the application of a sufficient inward fluid pressure to the check valve, to insure that it be opened and the fluid enter the cannula fluid flow passage.

Figure 2:
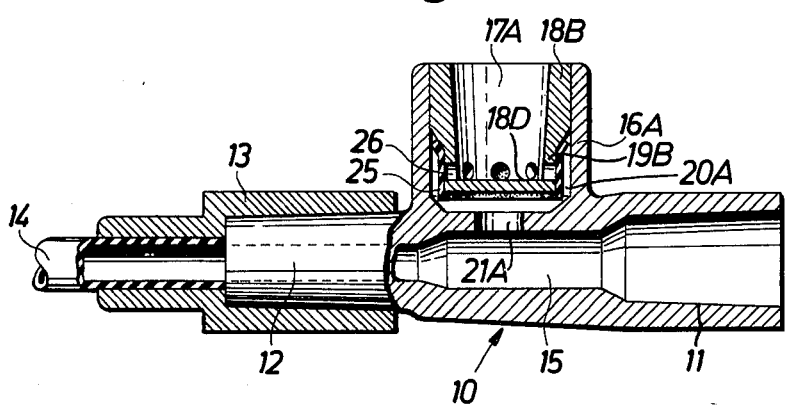

Two preferred embodiments of cannula assembly in accordance with the invention are shown in the drawings, in which:

FIG. 1 is a longitudinal section through one embodiment of cannula according to the invention, showing one form of cup-shaped inlet for introduction of a second fluid; and FIG. 2 shows in longitudinal section a second embodiment of cannula according to the invention with another form of cup.

In each of the embodiments shown in FIGS. 1 and 2, the check valve is in the form of a tube of resilient material, in sealing engagement with the outer surface of the inlet cup, covering over the side openings in the inlet cup communicating the cup with the main cannula flow passage 15.

The cannula shown in FIG. 1 comprises a housing 10 with a through fluid flow passage 15. The passage 15 at the inlet end 11 is conically shaped, for reception of the tapered end of a tube from an infusion fluid container or like receptacle for delivery of a first fluid to the cannula, such as an infusion fluid. At the other end of the passage 15 the cannula body 10 is shaped in a tapered tip 12, for connection to for example the connection nipple 13 of a catheter tube 14. The conical-and-tapered fit at 11 and 12 ensures a snug sealing engagement between the two connecting members at each joint. Although not shown in the drawing, the housing 10 can also be provided with one or two wings or flanges, to permit taping or other attachment of the housing to the skin of the patient, following insertion of the catheter 14 into (for example) a vein of the patient.

The fluid flow passage 15 has a second fluid inlet 21 at one side, about midway of the passage, through which a second fluid from a second source of supply (not shown) can be admitted to the passage, such as (for example) from an injection device, such as a hypodermic syringe. The inlet 21 is in fluid flow connection with the annular passage 20 surrounding a cup-shaped insert 18A, of hard material, such as plastic or metal, which rests in the socket 16 of the body 10. The inlet member 18A has a conical through passage 17, shaped to sealingly receive the outlet tip of the injection device, such as a hypodermic syringe. The conical passage 17 terminates in a ledge 18C, which serves to limit the insertion of the injection device, and continues as the passage 22 of considerably reduced diameter, extending within the tip portion 19 of the insert member 18A, also of considerably reduced diameter.

The sides of the tip portion 19 spaced from the walls of the socket 16 are provided with a plurality of laterally-extending outlet openings 23, which communicate the passage 22 with the passage 20. As shown in the drawing, there are two such passages, but any desired number can be provided, and only one outlet opening will also suffice.

The outlet openings 23 are closed off by the tubular check valve 24, which encloses the sides of tip portion 19. The valve tube 24 at one end bears internal threads 24A which engage corresponding external threads 19A on the base of tip 19, thus serving to hold the check valve in position on the tip.

The valve tube 24 is of a resilient material, such as silicone rubber, and while its normal tendency is to remain in the position shown in FIG. 1, closing off the openings 23, it can be deflected outwardly (since the lower end is free, and not attached to the tip) under a sufficient pressure of a fluid in the passage 22, and openings 23. When it opens under such pressure, fluid can pass from passage 22 through openings 23 into the passage 20, and then via the inlet opening 21 into the cannula passage 15. This occurs when for example the syringe piston of the hypodermic syringe is pushed in, after sealing insertion of the syringe tip in the conical passage 17.

It is apparent from the construction shown that the check valve 24 is not in alignment with the inlet opening of the insert 18A, or the passage 22. Thus, if the injection device is provided with a needle, the needle can enter the passage 22, but will strike the end wall 22A of the insert 18A. The insert is of hard material, such as plastic, and can accept the impact of a needle or other tip end of the injection device without damage. Thus, injury of the check valve is avoided by this construction.

In operation, the conical socket 11 would be attached to the tip of a delivery tube from a receptacle for a first fluid, such as an infusion container, whereupon such fluid will pass through the passage 15 into the catheter tube 14, and be administered to the patient. The check valve 24, being closed, prevents escape of such fluid via inlet 21 and passage 20.

Whenever administration of a second fluid is desired, the second fluid is filled into a suitable delivery device, such as a hypodermic syringe. The tip end of the syringe is inserted in the passage 17, and sealingly engaged with the conical walls of the passage, so that fluid can be injected under pressure into the passage. Such fluid fills the passage 22 and openings 23, and under delivery pressure from the delivery device opens the check valve 24, and then passes into the passage 20, and thence by the inlet 21 into the cannula passage 15, whence it also is administered to the patient via the catheter.

As soon as the second fluid has been administered, and fluid pressure in the passage 22 is reduced, the check valve 24 closes again, preventing escape of fluid from the infusion device entering via inlet 11 in passage 15 through the inlet 21 and passage 20.

The device shown in FIG. 2 is similar to that of FIG. 1 and consequently like reference numerals are used for like parts.

In this case the insert member 18B, which is of hard material such as metal or plastic, is of a somewhat different configuration. It does not have the ledge 18C, but is instead conically shaped throughout its length. The tip end 19B is of reduced diameter, defining passage 20A within the socket 16A. The conical passage 17A therethrough terminates at the end wall 18D at the tip end. The side walls of the insert are provided with a number of lateral openings 26, in this case eight, which communicate the passage 17A with the annular passage 20A on the outside of the tip 19B of the sealing insert. The passage 20A is in fluid flow connection with the fluid inlet 21A which leads to the cannula passage 15. In this case also, the check valve 25 is a tube of resilient material, such as silicone rubber, and extends about the outer periphery of the tip portion 19A, tightly engaging it, and sealing off the openings 26. Upon application of a sufficient fluid pressure in the insert passage 17A and openings 26, however, the check valve 25 is forced away from the openings, and fluid can then pass from the passage 17A via the openings 26 into the passage 20A, and thence via the inlet 21A into the main cannula passage 15.

In operation, the tip of the second fluid delivery device, such as a hypodermic syringe, is inserted in the conical passage 17A of the insert 18B, and the fluid then introduced under pressure into the passage, whereupon the check valve 25 is driven away from the opening 26, so that fluid can pass from the injection device through the passage 17A, openings 26, passage 20A, and inlet opening 21A, into the main cannula passage 15.

In this case also, any impact between the delivery tip end, such as a needle tip of a hypodermic syringe inserted in the passage 17A, is received by the end wall 18D, avoiding injury to the check valve 25.

While the cannula assembly of the invention can be made of any suitable material, it is normally desirable to make it of hard plastic such as polytetrafluoroethylene, polyamide, polyester, polycarbonate, and polystyrene, or metal, such as stainless steel or aluminum. If the materials are relatively inexpensive, the device can be thrown away after one use, thus avoiding the necessity of cleaning and sterilization before reuse, but of course this can be done if desired. The component parts of the device can readily be separated for cleaning and sterilization, since the insert members 18A 18B fit in the inlet opening in a press fit, and are easily removed. A press fit is quite sufficient since there are no high internal fluid pressures to be withstood.

Instead of a tubular or sleeve-type check valve, other types of check valves in or at the entry or outlet of the openings from the second fluid inlet to the main cannula passage can be used, such as umbrella valves (the umbrella is on the outside and the stem passes through the opening), flap valves, poppet valves and duckbill valves.

While the cannula assembly is shown in connection with a catheter, it will of course be understood that it can be connected to any kind of a fluid delivery of injection system. To facilitate connection to standard delivery systems, the first and second fluid inlets and the fluid outlet of the device can be provided with Luer-lok fittings, made to accept a standard Luer-lok fitting from the delivery devices to be attached thereto. Moreover, while it has been indicated that the two sources of supply are for example injection fluid and infusion fluid, any two sources of fluid supply can be interconnected by the device, provided that only in the case of the second fluid introduced via the second fluid inlet, a sufficient fluid pressure can be applied, as required, to open the check valve, and introduce the amount of fluid required for the desired purpose into the main cannula passage.

Having regard to the foregoing disclosure the following is claimed as the inventive and patentable embodiments thereof:

1. A cannula for administration of two fluids from two separate sources of fluid supply comprising, in combination, a housing; a fluid flow passage therethrough having first and second fluid inlets and one fluid outlet, at least one of the fluid inlets being socket-shaped and having an opening leading thereinto, side walls, and an end wall in alignment with the opening, to receive therewithin needle delivery means of a needle-tipped syringe for delivery of one of the fluids to the cannula fluid flow passage; and of a short enough depth so that the needle delivery means can impact against an end wall of the socket; an opening through a side wall of the one fluid inlet; and a check valve on the other side of the socket side wall and extending across the opening in the side wall, compelling flow therethrough only in the inward direction; the end wall of the one fluid inlet being in alignment with the socket opening accepting any impact of the delivery means when inserted in the socket opening and inhibiting impact injury to the check valve upon such insertion.

2. A cannula in accordance with claim 1, in which the socket is shaped to sealingly receive the delivery means of an injection device.

3. A cannula in accordance with claim 2, in which the injection device is a syringe.

4. A cannula in accordance with claim 1 in which the socket comprises a cup-shaped insert of hard material inserted in a socket in the housing and having side and end walls, with at least one fluid opening through at least one side wall.

5. A cannula in accordance with claim 4, in which the check valve is a resilient tube extending circumferentially about an end of the insert, and closing off all side wall openings therein.

6. A cannula in accordance with claim 5, in which the insert has an end portion of reduced diameter spaced from the socket walls, and over which the tubular check valve is disposed.

7. A cannula in accordance with claim 4 in which the insert has an inlet opening of relatively wide diameter terminating in a portion of constricted diameter with a peripheral ledge therebetween serving as a step restricting entry of the delivery means into the inlet opening.

8. A cannula in accordance with claim 4, in which the insert fits in the socket in a press fit.

9. A cannula in accordance with claim 1 in which the housing is in a T-shape having first, second and third arms, with fluid flow passages through each of the three arms of the T; the first arm having the first fluid inlet, for reception of a flow connection from a first source of fluid supply; the second arm having the second inlet, for reception of a flow connection from a second source of supply, and the third arm having the fluid outlet, for reception of a flow connection to delivery means for administration of fluids from the cannula.

10. A cannula in accordance with claim 1, formed of hard plastic material.

* * * * *

UNITED STATES PATENT OFFICE
CERTIFICATE OF CORRECTION

Patent No. 4,063,555      Dated December 20, 1977

Inventor(s)  Bjorn Ulinder

It is certified that error appears in the above-identified patent and that said Letters Patent are hereby corrected as shown below:

Column 1, line 48, insert --of the-- after "end", first occurrence.
Column 4, line 34, "of" should be --or--.

Signed and Sealed this

Fourth Day of July 1978

[SEAL]

Attest:

RUTH C. MASON
Attesting Officer

DONALD W. BANNER
Commissioner of Patents and Trademarks